(12) United States Patent
Pilarsky et al.

(10) Patent No.: US 7,667,037 B2
(45) Date of Patent: Feb. 23, 2010

(54) PROCESSES FOR PREPARATION OF ZIPRASIDONE

(75) Inventors: Gideon Pilarsky, Holon (IL); Natalia Shenkar, Petah-Tiqva (IL); Marioara Mendelovici, Rechovot (IL); Tamar Nidam, Yehud (IL); Anna Balanov, Rehovot (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 348 days.

(21) Appl. No.: 10/973,498

(22) Filed: Oct. 25, 2004

(65) Prior Publication Data

US 2005/0143397 A1 Jun. 30, 2005

Related U.S. Application Data

(60) Provisional application No. 60/514,096, filed on Oct. 24, 2003, provisional application No. 60/515,328, filed on Oct. 28, 2003.

(51) Int. Cl.
*C07D 237/14* (2006.01)
*C07D 237/04* (2006.01)
*C07D 417/14* (2006.01)
*C07D 401/14* (2006.01)

(52) U.S. Cl. ............ 544/366; 544/230; 544/237; 544/284; 544/359; 544/363; 544/373

(58) Field of Classification Search ............ 544/230, 544/237, 284, 359, 363, 366, 373
See application file for complete search history.

(56) References Cited

U.S. PATENT DOCUMENTS

| 4,831,031 | A | 5/1989 | Lowe, III et al. |
|---|---|---|---|
| 5,206,366 | A | 4/1993 | Bowles |
| 5,312,925 | A | 5/1994 | Allen et al. |
| 5,338,846 | A | 8/1994 | Busch et al. |
| 5,359,068 | A | 10/1994 | Urban |
| 6,110,918 | A | 8/2000 | Busch et al. |
| 6,111,105 | A | 8/2000 | Fox et al. |
| 6,150,366 | A | 11/2000 | Arenson et al. |
| 2002/0016498 | A1 | 2/2002 | Am Ende et al. |
| 2004/0048876 | A1 | 3/2004 | Busch et al. |

FOREIGN PATENT DOCUMENTS

| EP | 0 584 903 | A1 | 3/1994 |
|---|---|---|---|
| EP | 0 586 181 | A2 | 3/1994 |
| EP | 0 965 343 | A2 | 12/1999 |
| EP | 0 965 343 | B1 | 12/1999 |
| EP | 1157726 | A1 | 11/2001 |
| WO | WO 97/42191 | | 11/1997 |
| WO | WO 00/59489 | | 10/2000 |
| WO | WO 00/59489 | A3 | 10/2000 |
| WO | WO 00/72847 | | 12/2000 |
| WO | WO 01/91756 | A2 | 12/2001 |
| WO | WO 01/91756 | A3 | 12/2001 |
| WO | WO-03/070246 | | 8/2003 |
| WO | WO 03/070246 | A1 | 8/2003 |
| WO | WO 2004/050655 | | 6/2004 |
| WO | WO 2004/054621 | | 7/2004 |
| WO | WO 2004/070246 | | 8/2004 |
| WO | WO 2004/089948 | | 10/2004 |

OTHER PUBLICATIONS

*J. Phys. D: Appl. Phys.* 26 (Aug. 14, 1993) B181-B187.
EL Parrott, in *Pharmaceutical Techology: Fundamental Pharmaceutics*, Burgess, Minneapolis, Minn., 1970, pp. 1-36.
EL Parrott, *Pharm. Manuf.*, 2, 30-37 (1985).
SL Lowell and JE Shields, *Powder Surface Area and Porosity*, Chapman and Hall New York, 1984.
S. Brunauer, PH Emmett and E Teller, *J.Am.Chem. Soc.*, 6, 309 (1938).

*Primary Examiner*—James O Wilson
*Assistant Examiner*—Ebenezer Sackey
(74) *Attorney, Agent, or Firm*—Kenyon & Kenyon LLP

(57) ABSTRACT

Provided are processes for preparing ziprasidone from CEI and BIPT.

37 Claims, 1 Drawing Sheet

| EXP. | | ADDITIVE | TEMP. | TIME | BITP | CEI | ZPR | Obs. |
|---|---|---|---|---|---|---|---|---|
| | | | | | 0.28 | 0.80 | 1.0 | |
| 1 | REACTION MIXTURE | | 100°C | 14h | 16.8 | 7.1 | 71.6 | US'846 |
| | REACTION MIXTURE | | | 16h | 15.9 | 6.6 | 66.6 | |
| | SOLID | | | | 1.9 | 5.25 | 81.7 | |
| 2 | REACTION MIXTURE | | | 16h | 7.3 | 0.3 | 71.9 | US'846 |
| | SOLID | | | | 3.5 | | 90.5 | |
| 3 | REACTION MIXTURE | Na$_2$SO$_4$ | 100°C | 5h | 26.5 | 16.3 | 49.4 | |
| | | | | 9h | 11.9 | 9.2 | 70.9 | |
| | SOLID | | | | | | 86.9 | |
| 4 | REACTION MIXTURE | NaCl | 95°C | 7h | 21.0 | 11.6 | 60.3 | |
| | | | | 26h | 13.9 | 0/4 | 78.0 | |

THE MOLAR RATIO OF THE IONIC ADDITIVE IS ~5–6 EQ. TO BITP HCl. PREFERRED AMOUNT OF THE ADDITIVE IS AT LEAST EQUIVALENT AMOUNT.

FIG. 1

PROCESSES FOR PREPARATION OF ZIPRASIDONE

RELATED APPLICATIONS

This application claims the benefit of U.S. provisional application Ser. Nos. 60/514,096, filed Oct. 24, 2003, and 60/515,328, filed Oct. 28, 2003, the contents of all of which are incorporated herein.

FIELD OF THE INVENTION

The present invention relates to processes for preparation of ziprasidone.

BACKGROUND OF THE INVENTION

Ziprasidone is an antipsychotic agent that is chemically unrelated to phenothiazine or butyrophenone antipsychotic agents. Ziprasidone has the following chemical name 5-[2-[4-(1,2-benzisothiazol-3-yl)-1-piperazinyl]ethyl]-6-chloro-1,3-dihydro-2H-indol-2- and structure:

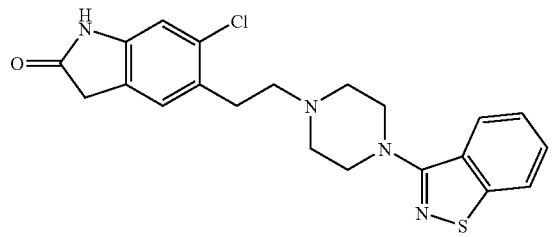

Ziprasidone is administered to a host such as a mammal, preferably a human, for treatment of psychiatric disorders such as schizophrenia. Other uses for ziprasidone are disclosed in WO 03/070246, WO 01/91756, incorporated herein by reference. A process for preparation of ziprasidone HCl monohydrate having a mean particle size equal to or less than about 85 microns is also disclosed in U.S. Pat. No. 6,150,366 and EP 0 965 343 A2.

Ziprasidone has been marketed under the name GEODON as an oral capsule and as an injectable drug. GEODON capsules contain the monohydrate hydrochloride salt of ziprasidone, and come in 20, 40, 60 and 80 mg dosage forms. GEODON for injection contains a lyophilized form of ziprasidone mesylate trihydrate, and contains 20 mg base equivalent of ziprasidone.

A process for preparing Ziprasidone ("ZPR") like compounds is disclosed in U.S. Pat. No. 4,831,031. In example 16 of the '031 patent, ziprasidone is prepared by nucleophilic reaction between 1,2-Benzisothiazole-3-piperazinyl ("BITP") and 5-(2-chloroethyl)-6-chloro-1,3-dihydro-indole-2(2H)-one ("CEI") in methyl-iso-butyl-ketone with $Na_2CO_3$ as a base and in the presence of a catalytic amount of sodium iodide ("NaI"). The yield provided is ~20% after chromatography of the crude reaction product.

U.S. Pat. Nos. 5,206,366 and 5,338,846 disclose a process for preparing ziprasidone which react BITP free base or its hydrochloride salt with CEI in water in the absence of an organic solvent. In example 1 of the '846 patent, a solution of sodium carbonate in 5 volumes of water is mixed with CEI and BITP hydrochloride. The mixture is then stirred and heated to reflux for 13 hours and slurried at room temperature for 1 hour. The product is then subjected to subsequent workup. The crude is purified by slurry in iso-propyl alcohol ("IPA") and crystallized from tetrahydrofuran ("THF"). The yield is 83.8% (reaction+crystallization) and the purity of the crystallized solid is 99.7%.

In Example 1 of the '366 patent, ziprasidone is prepared from a reaction mixture of BITP free base in 5 volumes of water, sodium carbonate and CEI at 100° C. for 16 hours in the absence of an organic solvent. After approximately 16 hours of reflux, the reaction mixture is cooled to room temperature, stirred for approximately one hour and then filtered. The crude product obtained has a 91% yield and a purity of 94.5%.

In section entitled "experiment" of U.S. Pat. No. 5,312,925 (EP 05686191), a solution of carbonate in 5 volumes of water is mixed with BITP and CEI, and the resulting slurry is heated at reflux for 14 hours. The reaction mixture is then cooled and filtered. The wet product is then re-slurried in isopropyl alcohol at room temperature for 2 hours.

In page 35 of WO 03/070246 ziprasidone having a low des-chlorinated impurity content is prepared by reacting CEI with BITP in water in the presence of carbonate at reflux temperature for about one day. After cooling, the resulting solid is slurried in isopropanol and recrystallized from THF. The level of the impurity is controlled by purification of CEI before reaction.

WO 01/91756 discloses a derivative of ziprasidone which is called s-methyl-dihydro-ziprasidone. The only example provided uses dihydro-ziprasidone as starting material.

WO 00/59489 discloses metabolites of ziprasidone, particularly ziprasidone sulfoxide and ziprasidone sulfone. The examples provided in WO 00/59489 are in the present tense, i.e., prophetic. Ziprasidone is prepared in WO 00/59489 substantially as in U.S. Pat. No. 4,831,031. The sulfoxide and sulfone are then obtained from ziprasidone by oxidation with peroxide.

WO 00/72847 discloses a pharmaceutical composition of ziprasidone containing ziprasidone free base or a pharmaceutically acceptable ziprasidone acid addition salt, water, polysorbate, a viscosity agent, and colloidal silicon dioxide.

Reaction of BITP with CEI often results in impurities and low yields, including impurities resulting from BITP and CEI that is not consumed. Other than in water, a suitable organic solvent has been difficult to find for reaction of BITP with CEI. Form example, in U.S. Pat. No. 4,831,031, where MIK was used, only a 20% yield was obtained. There is a need in the art for organic solvents to carry the reaction between CEI and BITP.

Even with reactions that take place in water, repetition of these reactions leads to BITP not being consumed and being present as much as 10 times the level of CEI as area percentage HPLC. A disparity in the level of CEI to BITP remaining is problematic since the BITP remaining can no longer react if the CEI has been consumed. The BITP remaining becomes an impurity and results in a decrease in yield. There is a need in the art for additional processes for preparation of ziprasidone which increase the yield of the process and consume most of the BITP and CEI.

SUMMARY OF THE INVENTION

In one embodiment, the present invention provides a process for preparing ziprasidone comprising the steps of reacting BITP or a salt thereof with CEI in water in the presence of a base and a non-basic ionic additive to obtain ziprasidone, and recovering the ziprasidone.

In another embodiment, the present invention provides a process for preparing ziprasidone comprising the step of reacting BITP or a salt thereof with CEI in a reaction mixture of a base and water, wherein an organic solvent is added to the reaction mixture to accelerate the reaction rate or improve the purity profile.

In another embodiment, the present invention provides a process for preparing ziprasidone comprising the step of reacting BITP or a salt thereof with CEI in glycerol in the presence of a base, and recovering the ziprasidone.

In another embodiment, the present invention provides a process for preparing ziprasidone comprising the steps of reacting BITP or a salt thereof with CEI in a polar organic solvent in the presence of a base and more than 0.5 molar of a promoter to obtain ziprasidone, and recovering the ziprasidone.

In another embodiment, the present invention provides a process for preparing ziprasidone comprising the steps of reacting BITP or a salt thereof with CEI in sulfolane in the presence of a base, and recovering the ziprasidone.

In another embodiment, the present invention provides a process for preparing ziprasidone comprising the steps of reacting BITP or a salt thereof with CEI in toluene in presence of a base, and recovering the ziprasidone.

In another embodiment, the present invention provides a process for preparing ziprasidone comprising the steps of reacting BITP or a salt thereof with CEI, and recovering the ziprasidone, wherein the reacting is carried out with sodium carbonate decahydrate at a temperature greater than melting point of sodium carbonate decahydrate but lower than melting point of sodium carbonate anhydrous.

In another embodiment, the ziprasidone is converted to a pharmaceutically acceptable salt thereof, preferably the HCl salt.

BRIEF DECRIPTION OF THE FIGURE

FIG. 1 provides a comparative example of reactions carried out by the '846 patent and the present invention.

DETAILED DESCRIPTION OF THE INVENTION

As used herein, the term "CEI" refers to 5-(2-chloroethyl)-6-chloro-1,3-dihydro-indole-2(2H)-one. As used herein, the term "BITP" refers to 1,2-Benzisothiazole-3-piperazinyl.

The present invention provides processes suitable for the preparation of ziprasidone. These processes may be suitable for industrial production. The present invention discloses organic solvents that provide a suitable yield for reaction of CEI with BITP, specifically toluene, sulfolane (thiocyclopentane-1,1-dioxide), n-butanol and glycerol. Sodium carbonate is soluble in all four solvents, while CEI is not, thus providing a slurry reaction where the base does not deteriorate CEI. These solvents have been obtained after an extensive and difficult search, since most other organic solvents resulted in limited yield. In addition to discovering of organic solvents for such process, various manners to improve the process as carried out in water have been discovered.

In one embodiment, the present invention provides for preparing ziprasidone by reacting BITP or BITP salt with CEI in water in the presence of a base and non-basic ionic additive. As used herein, the term "non-basic ionic additive" refers to water soluble salts whose dissolution in water does not result in a base. Examples of such additives include chloride (halide) (associated with hydrochloric acid), nitrate (associated with nitric acid) and sulfate (associated with sulfuric acid) salts. Preferred salts include alkali and alkaline earth salts, such as sodium chloride and sodium sulfate. The term however does not include sodium iodide. An example of a basic salt reagent is sodium carbonate, whose anion carbonate, is basic. Preferably the temperature of the reaction is about 80° C. to about reflux, with about reflux temperature being preferred. A base is used in this embodiment in addition to the non-basic inorganic salt reagent in order to increase the reaction rate. In a preferred embodiment, the base is added portion-wise, i.e., at least in two separate portions at separate times, more preferably, at least in four separate portions at separate times. A preferred base is sodium or potassium carbonate.

FIG. 1 provides a comparative example where reactions are carried out as in the '846 patent, and in the presence of non-basic inorganic salts. With sodium sulfate, the reaction after 9 hours provided better results than in its absence after 16 hours. In the presence of sodium sulfate, the amount of CEI and BITP (HPLC area percentage) remaining after 9 hours is the same. However, in the absence of sodium sulfate, a 3:1 ratio (HPLC area percentage) of BITP to CEI remained, which makes it difficult to consume all of the BITP since there is not enough CEI remaining to react with BITP.

The present invention also provides for synthesis of ziprasidone by reacting BITP or BITP salt with CEI in the presence of a base, in a mixture of about a 9:1 water and organic solvent (v/v). An addition of about 5% to about 15%, more preferably about 10% by volume n-butanol results in substantially most of BITP and CEI being consumed. Preferably, the organic solvent is selected from the group consisting of $C_1$-$C_5$ alcohols. More preferably, the alcohol is n-butanol. While in the absence of n-butanol, much of BITP remains unconsumed, most of the CEI has been consumed. In a preferred embodiment, the base is added portion-wise, i.e., at least in two separate portions at separate times, more preferably, at least in four separate portions at separate times. Comparative experiments are shown in Table I:

TABLE I (carried out in presence of sodium carbonate)

| Exp. | | Solvent | Time | HPLC Area Percentage | | |
| --- | --- | --- | --- | --- | --- | --- |
| | | | | BITP | CEI | ZPR |
| 1 | Reaction mixture | Water | 15 h | 14.5 | 2.16 | 79.7 |
| | Solid | | | | | 94.22 |
| 2 | Reaction mixture | Water:n-BuOH 9:1 | 35 h | 2.8 | 0.66 | 88.03 |
| | Solid | | | 1.9 | 0.5 | 93.6 |
| 3 (Ex. 3) | Reaction mixture | Water:n-BuOH 8:2 | 25 h | 13.1 | 3.8 | 74.8 |
| | Solid | | | | | 90.77 |
| 4 (Ex. 4) | Reaction mixture | Water:n-BuOH 7:3 | 28 h | 12.7 | 3.5 | 78.1 |
| | Solid | | | | | 98.11 |

In another aspect, the present invention provides for preparing the ziprasidone in glycerol in the presence of a base, optionally in the presence of a non-basic ionic additive. The bases used are organic or inorganic bases that are soluble in glycerol, such as $Na_2CO_3$. In a preferred embodiment, the base is added portionwise, i.e., at least in two separate portions at separate, more preferably, at least in four separate portions at separate times. Preferably the temperature during reaction is from about 80° C. to about 140° C., more preferably from about 100° C. to about 120° C. The reaction takes place faster when carried out in glycerol than when carried out only in water. Glycerol is one of the few organic solvents that we found suitable for such reaction. Examples are illustrated in Table II:

TABLE II

| Exp. Nr. | Solvent | Base | Time | HPLC Area Percentage | | | | |
|---|---|---|---|---|---|---|---|---|
| | | | | BITP | CEI | ZPR | 1.4 | 1.59 |
| 1 (Ex. 2) Reaction mixture | Glycerol | $Na_2CO_3$ | 1 h 45' | 11.75 | 4.3 | 64.8 | | |
| Solid | | | | 2.7 | 1.2 | 89.03 | 1.2 | 0.6 |
| 2 Reaction mixture | Glycerol | $Na_2CO_3$ | 9 h | 4.6 | 5.3 | 75.9 | 1.5 | 0.9 |
| Solid | | | | 0.9 | 0.55 | 89.8 | 1.5 | 1.5 |

The present invention also provides for preparing ziprasidone in a polar solvent such as a $C_1$ to $C_5$ alcohol, or glycols (including glycol ethers) in the presence of a base with an amount of a promoter that is higher than a catalytic amount, e.g., at least about 50% of molar equivalent, more preferably one equivalent. Preferably, the alcohol is n-butanol, iso-butanol, 1-pentanol or any of the isomers of amylalcohol. A glycol ether may also be used, preferably of or less than $C_{12}$, more preferably of or less than $C_6$. In a preferred embodiment, the base is added portion-wise, i.e., at least in two separate portions at separate times, more preferably, at least in four separate portions at separate times. A promoter is a chemical which itself is a feeble catalyst, but greatly increases the activity of a given catalyst, which herein is a base. By polar solvent, it is meant a solvent having a polarity index of equal or greater than that of n-butanol, 4.0. Examples of such promoters include sodium and potassium bromide/iodide. In a preferred embodiment, an about a one equivalent of NaI is used as the reaction promotor. When NaI is used in an ~equivalent amount or more, as supposed to a catalytic amount, the conversion is higher and the reaction purity profile is significantly improved compared to using $Na_2CO_3$ alone. The temperature for the reaction is preferably of about 80° C. to about 140° C., more preferably from about 100° C. to about 120° C. The comparative Examples for the preparation of ziprasidone in n-butanol are shown in table III:

TABLE III

| | | | (HPLC Area Percentage) | | | | |
|---|---|---|---|---|---|---|---|
| Exp. Nr. | NaI, eq. | Eq. CEI | Time | BITP | CEI | ZPR | 1.4 | 1.59 |
| 1 | 20% molar | 1.5 | 25 h | 7.8 | 10.7 | 76.6 | | |
| 2 | 0.9 mol | 1.5 | 8.5 h | 0.3 | 1.05 | 86.3 | 0.5 | 0.4 |

In another aspect, the present invention provides for reacting BITP or its salt with CEI in sulfolane in the presence of a base to obtain ziprasidone. The reaction is preferably carried out at a temperature of about 70° C. to about 140° C., more preferably from about 75° C. to about 120° C., and most preferably from about 85° C. to about 110° C. The reaction is preferably carried out in the presence of a promotor such as NaI, NaBr, KBr or KI. The quantity of the promoter is preferably of about 20% to about 100% molar ratio compared to the reactants. In a preferred embodiment, the base is added portion-wise, i.e., at least in two separate portions at separate times, more preferably, at least in four separate portions at separate times.

In another aspect, the present invention provides for reacting BITP or its salt with CEI in toluene in the presence of a base to obtain ziprasidone. The reaction is preferably carried out in the presence of a promoter such as NaI, NaBr, KBr or KI. A preferred promoter is NaI, which is preferably used from about 0.3 to about 2 equivalents, more preferably from about 0.5 to about 1.5 eq. equivalents, and most preferably about 1 equivalent. The reaction is preferably carried out at a temperature of about 70° C. to about reflux temperature, more preferably from about 85° C. to about reflux temperature, and most preferably at reflux temperature. The reaction is carried out in the presence of a base, preferably $Na_2CO_3$. In a preferred embodiment, the base is added portion-wise, i.e., at least in two separate portions at separate times, more preferably, at least in four separate portions at separate times.

Bases are often used in preparation of ziprasidone to accelerate the reaction between BITP and CEI. One reaction aspect to consider for industrial scale is the reactivity of the starting material, CEI, to the basic reactions conditions. The low solubility of the base or the CEI in the solvent is an advantage because it makes the separation of the base from the CEI easier, i.e., a preferred solvent is a solvent in which one of CEI or the base is not soluble. For example CEI is not soluble in glycerol while the base $Na_2CO_3$ is partially soluble. If CEI and the base are both soluble in the reaction mixture, CEI may decompose into a side product and may increase the amount of impurities. The addition of the base in portions further protects CEI by preventing base excess in respect to CEI. By portion-wise, it is meant that the base is added in separate portions, at least two, more preferably about 4 portions. The subsequent portion is added when the previous portion has been consumed to a suitable degree. The present invention also provides for keeping the amount of base low relative to CEI by maintaining a substantially constant level of the base through continuous feeding.

In another embodiment, the present invention provides for using sodium carbonate decahydrate as a base. The melting point of sodium carbonate decahydrate is much lower that sodium carbonate anhydrous, thus allowing the reaction to proceed with liquid sodium carbonate rather than solid.

After the above reactions, ziprasidone may be recovered by conventional techniques such as filtration, centrifugation, decanting, etc. The recovered product may be washed with a suitable solvent, or further slurried or recrystallized from a solvent. A suitable solvent for slurry is a $C_1$ to $C_4$ alcohol such as isopropanol. A suitable solvent for recrystallization is THF.

The methods of the present invention may be carried out in such way to reduce the des-chlorinated impurities present in the final product. The starting chlorinated reactants may be purified to eliminate des-chlorinated impurities as disclosed in WO 03/070246, incorporated herein by reference. Preferably, the CEI used has a dechlorinated content of less than about 0.3%, more preferably less than about 0.15%, and most preferably less than about 0.03% as calculated by the method of WO 03/070246. Preferably the ziprasidone obtained has a dechlorinated content of less than about 1000 ppm, more preferably less than about 500 ppm and most preferably less than about 100 ppm, as calculated by the method of WO 03/070246.

The process of the present invention may also be used to prepare the ziprasidone sulfone or sulfoxide of WO 00/59489 by oxidizing the ziprasidone prepared.

The ziprasidone recovered may be converted to ziprasidone HCl hemihydrate as disclosed in U.S. Pat. No. 4,831,031, Example 16 (column 13, line 13). Ziprasidone HCl monohydrate is disclosed in U.S. Pat. No. 5,312,925 and EP 0 586 181 A1. The monohydrate is characterized by XRD, IR and water content. It is reported that the water content of the monohydrate ranges from 3.8 to 4.5% by weight. The ziprasidone HCl monohydrate is prepared from ziprasidone base anhydrous. Additionally, the ziprasidone prepared may be converted to one of the polymorphic forms disclosed in currently pending provisional applications No. 60/475,806, filed Jun. 3, 2003, No. 60/487,913, filed Jul. 16, 2003 and No. 60/494,970, filed Aug. 13, 2003. All these patents and applications are incorporated herein by reference.

Additionally, the product may be converted to a pharmaceutically acceptable salt such as a mesylate salt. The mesylate salts of ziprasidone, including monohydrate and trihydrate, are disclosed in U.S. Pat. Nos. 6,110,918 and 5,245,765.

The pharmaceutical formulations of the present invention contain crystalline and/or amorphous polymorphic forms of a pharmaceutically acceptable salt of ziprasidone. In addition to the active ingredient(s), the pharmaceutical formulations of the present invention may contain one or more excipients. Excipients are added to the formulation for a variety of purposes.

Diluents increase the bulk of a solid pharmaceutical composition, and may make a pharmaceutical dosage form containing the composition easier for the patient and care giver to handle. Diluents for solid compositions include, for example, microcrystalline cellulose (e.g. beta form and Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®) and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc and zinc stearate.

Flavoring agents and flavor enhancers make the dosage form more palatable to the patient. Common flavoring agents and flavor enhancers for pharmaceutical products that may be included in the composition of the present invention include maltol, vanillin, ethyl vanillin, menthol, citric acid, fumaric acid, ethyl maltol and tartaric acid.

Solid and liquid compositions may also be dyed using any pharmaceutically acceptable colorant to improve their appearance and/or facilitate patient identification of the product and unit dosage level.

In liquid pharmaceutical compositions of the present invention, ziprasidone and any other solid excipients are dissolved or suspended in a liquid carrier such as water, vegetable oil, alcohol, polyethylene glycol, propylene glycol or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention include, for example, gelatin, egg yolk, casein, cholesterol, acacia, tragacanth, chondrus, pectin, methyl cellulose, carbomer, cetostearyl alcohol and cetyl alcohol.

Liquid pharmaceutical compositions of the present invention may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth and xanthan gum.

Sweetening agents such as sorbitol, saccharin, sodium saccharin, sucrose, aspartame, fructose, mannitol and invert sugar may be added to improve the taste.

Preservatives and chelating agents such as alcohol, sodium benzoate, butylated hydroxy toluene, butylated hydroxyanisole and ethylenediamine tetraacetic acid may be added at levels safe for ingestion to improve storage stability.

According to the present invention, a liquid composition may also contain a buffer such as guconic acid, lactic acid, citric acid or acetic acid, sodium guconate, sodium lactate, sodium citrate or sodium acetate. Selection of excipients and the amounts used may be readily determined by the formulation scientist based upon experience and consideration of standard procedures and reference works in the field.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, the most preferred route of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and losenges, as well as liquid syrups, suspensions and elixirs.

The dosage form of the present invention may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

The active ingredient and excipients may be formulated into compositions and dosage forms according to methods known in the art.

A composition for tableting or capsule filling may be prepared by wet granulation. In wet granulation, some or all of the active ingredients and excipients in powder form are blended and then further mixed in the presence of a liquid, typically water, that causes the powders to clump into granules. The granulate is screened and/or milled, dried and then screened and/or milled to the desired particle size. The granulate may then be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention may comprise any of the aforementioned blends and granulates that were described with reference to tableting, however, they are not subjected to a final tableting step.

When preparing injectable (parenteral) pharmaceutical compositions, solutions and suspensions are sterilized and are preferably made isotonic to blood. Injection preparations may use carriers commonly known in the art. For example, carriers for injectable preparations include, but are not limited to, water, ethyl alcohol, propylene glycol, ethoxylated isostearyl alcohol, polyoxylated isostearyl alcohol, and fatty acid esters of polyoxyethylene sorbitan. One of ordinary skill in the art can easily determine with little or no experimentation the amount of sodium chloride, glucose, or glycerin necessary to make the injectable preparation isotonic. Additional ingredients, such as dissolving agents, buffer agents, and analgesic agents may be added.

The solid compositions of the present invention include powders, granulates, aggregates and compacted compositions. The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages can be conveniently presented in unit dosage form and prepared by any of the methods well-known in the pharmaceutical arts.

The formulations of the present invention may contain other psychiatric drugs such as sertraline, paroxetine, fluoxetine, etc.

The dosage of GEODON may be used as a guidance. The oral dosage form of the present invention is preferably in the form of an oral capsule having a dosage of from about 10 mg to about 160 mg, more preferably from about 20 mg to about 80 mg, and most preferably capsules of 20, 40, 60 and 80 mg.

HPLC Conditions:

Column-C8

Mobile phase-Gradient of Ammonium acetate with methanol

Flow-1 ml/min

Detection-UV at 242 nm

Injection volume-100 ml

Sample concentration-0.04 mg/ml

EXAMPLES

1. Preparation of ZPR in n-BuOH with 0.9 mol NaI

In a three necked flask was charged n-BuOH (50 ml) and 1,2-Benzisothiazole-3-piperazinyl hydrochloride (BITP HCl) (5.6 g, 0.022 mol), and the obtained slurry was heated at 100° C. To the slurry, $Na_2CO_3$ (11.6 g), NaI (3 g) and 5-(2-chloroethyl)-6-chloro-1,3-dihydro-indole-2(2H)-one (CEI) (7.5 g, 0.032 mol) were added at 110° C.

The heating was maintained for 8.5 h. After cooling the reaction product was filtrated, washed with hexane and water, and dried at 60° C. The dried product weights 8.12 g and has an HPLC purity 92.7%.

2. Preparation of ZPR in Glycerol

In a three necked flask was charged BITP HCl (25 g, 0.098 mol), glycerol (62 ml), $Na_2CO_3$ (13 g) and the mixture was stirred for 10 minutes. CEI (5.9 g) was added and the reaction mixture was heated for 3 h at 115-120° C. After 3 h, the reaction was almost complete; after cooling to room temperature the solid was filtrated and was triturated in water and dried. The dried solid weights 42 g and the purity was 89.03%.

3. Preparation of ZPR in Water/$Na_2CO_3$/$Na_2SO_4$

In a three necked flask was charged BITP HCl (10 g), CEI (10.35 g) $Na_2CO_3$ (14.1 g), $Na_2SO_4$ (40 g) and water (50.7 g) and the reaction mixture was heated at reflux for 9 hours. After 9 hours reflux, the ziprasidone peak is 71% area from the reaction mixture.

4. Preparation of ZPR in Water Containing 10% n-BuOH

In a three necked flask was charged BITP HCl (4.9 g), $Na_2CO_3$ (6.91 g), CEI (4.68 g), water (25 ml) and n-BuOH (2.5 ml), and the mixture was heated. After about 20 hours reflux, ziprasidone was 75.5% area from the reaction mixture, and after 35 h reflux the conversion to ZPR was 88%. The solid was filtrated from the reaction mixture, washed with water and dried. The HPLC purity of the product was 93.6% area.

5. Preparation of ZPR in the Melt of $Na_2CO_3$ Decahydrate

To the melt of $Na_2CO_3$ decahydrate (40 g) was added BITP HCl (10 g) and CEI (10.35 g) and the mixture was heated at 95° C. for 10 hours. After 10 h the conversion to ZRP was 88.2% (% area by HPLC). To the reaction mixture water was added and the solid was filtrated and washed with water. After drying the solid weighs 17.14 g (purity by HPLC 88%).

6. Preparation of ZPR in the Presence of $Na_2SO_4$

In a 250 g three necked flask was charged water (25 ml), $Na_2CO_3$ (6.91 g), $Na_2SO_4$ (19.72 g), BITP HCl (4.9 g) and CEI (4.68 g). The mixture was stirred at ~100° C. for 12 hours. The isolated solid weights after drying 7.77 g (purity by HPLC 85.15%).

7. Preparation of ZPR in the Presence of NaCl

In a three necked flask was charged 40 ml brine, BITP HCl (14.1 g), CEI (10.35 g) and $Na_2CO_3$ (14.1 g); the mixture was than heated at 90° C. for 16 hours. After this the mixture was cooled, water was added and the solid was filtrated, washed with water and dried. The product weights after drying 16.9 g (purity by HPLC 87.5%).

8. Preparation of ZPR in Glycerol by $Na_2CO_3$ Portion-Wise Addition

To a three necked flask was charged BITP HCl (15 g), CEI (16.2 g), glycerol (60 ml) and $Na_2CO_3$ (3.11 g, 0.5 mol). The reaction mixture was heated at 115° C. and after 15' a new portion of 0.12 mol $Na_2CO_3$ was added. The heating was continued by addition of 0.12 mol base each hour. After 5 hours the base addition was completed and the reaction mixture was heated for an additional hour. After cooling to room temperature, the mixture was diluted with water (120 ml) and after 1 hour stirring the product crude was filtrated, washed with water and dried at 50° C. to afford 25.7 g dried product (yield 82.4%) (purity by HPLC 94%).

9. Preparation of ZPR in Sulfolane

In a three necked flask was charged: BITP HCl (5.14 g, 20 mmol), $Na_2CO_3$ (2.33 g, 22 mmol), NaI (3 g, 20 mmol) and sulfolane (20 ml). The mixture was heated at 90oC and than CEI (5.29 g, 23 mmol) was added with more sulfolane (10 ml); the reaction mixture was maintained at 90° C. for 4.5 h. The mixture was cooled to the room temperature and THF was added (150 ml); the solid was filtrated and washed with THF. From the mother liquors a second crop was obtained by precipitation with water. The yield of the two crops is 70% (purity by HPLC 98.4%).

10. Preparation of Ziprasidone in Toluene

In a 250 ml three necked flask was charged BITP HCl (5 g), $Na_2CO_3$ (6.5 g), CEI (5 g), NaI (1.5 g) and toluene (30 ml); the mixture was heated at reflux for 22.5 hours. After cooling to the room temperature the reaction product was filtrated, washed with methanol and triturated in water. After drying the product weights 7.27 g (yield 86%, purity by HPLC 98.3%).

Having thus described the invention with reference to particular preferred embodiments and illustrative examples, those in the art can appreciate modifications to the invention as described and illustrated that do not depart from the spirit and scope of the invention as disclosed in the specification. The Examples are set forth to aid in understanding the invention but are not intended to, and should not be construed to, limit its scope in any way. The examples do not include detailed descriptions of conventional methods. Such methods are well known to those of ordinary skill in the art and are described in numerous publications.

What is claimed is:

1. A process for preparing ziprasidone comprising the steps of reacting BITP or a salt thereof with CEI in water in the presence of a base and a non-basic ionic additive to obtain ziprasidone, and recovering the ziprasidone; wherein the non-basic ionic additive is other than sodium iodide.

2. The process of claim 1, wherein the ionic additive has an alkali metal or alkaline earth metal cation.

3. The process of claim 2, wherein the ionic additive is selected from the group consisting of nitrates, halides and sulfates.

4. The process of claim 3, wherein the ionic additive is sodium sulfate.

5. The process of claim 1, wherein the temperature of the reaction is about 80° C. to about reflux temperature.

6. The process of claim 5, wherein the temperature of the reaction is about reflux temperature.

7. The process of claim 1, wherein the base is sodium carbonate or potassium carbonate.

8. The process of claim 1, wherein the base is added portion-wise.

9. A process for preparing ziprasidone comprising the step of reacting BITP or a salt thereof with CEI in glycerol in the presence of a base, and recovering the ziprasidone.

10. The process of claim 9, wherein the process further comprises a non-basic ionic additive.

11. The process of claim 9, wherein the base is an organic base.

12. The process of claim 9, wherein the base is an inorganic base.

13. The process of claim 9, wherein the reaction is carried out at a temperature from about 80° C. to about 140° C.

14. The process of claim 13, wherein the temperature is from about 100° C. to about 120° C.

15. The process of claim 9, wherein the base is added portion-wise.

16. A process for preparing ziprasidone comprising the steps of reacting BITP or a salt thereof with CEI in a polar organic solvent in the presence of a base and more than 0.5 molar equivalent of a promoter to obtain ziprasidone, and recovering the ziprasidone.

17. The process of claim 16, wherein the base is added portion-wise.

18. The process of claim 16, wherein the organic solvent is a $C_1$ to $C_5$ alcohol.

19. The process of claim 18, wherein the alcohol is n-butanol or iso-butanol.

20. The process of claim 18, wherein the alcohol is amyl-alcohol or iso-amyl-alcohol.

21. The process of claim 16, wherein the organic solvent is glycol.

22. The process of claim 16, wherein the reaction temperature is from about 80° C. to about 140° C.

23. The process of claim 22, wherein the temperature is from about 100° C. to about 120° C.

24. A process for preparing ziprasidone comprising the steps of reacting BITP or a salt thereof with CEI in sulfolane in the presence of a base, and recovering the ziprasidone.

25. The process of claim 24, wherein the reacting is carried out at a temperature from about 70° C. to about 140° C.

26. The process of claim 25, wherein the temperature is from about 75° C. to about 120° C.

27. The process of claim 26, wherein the temperature is from about 85° C. to about 110° C.

28. The process of claim 24, wherein the molar ratio of the promoter is of about 20% to about 100% compared to BITP or CEI.

29. The process of claim 24, wherein the base is added portion-wise.

30. A process for preparing ziprasidone comprising the steps of reacting BITP or a salt thereof with CEI in toluene in presence of a base, and recovering the ziprasidone.

31. The process of claim 30, wherein the reaction is carried out at a temperature of about 70° C. to about reflux temperature.

32. The process of claim 31, wherein the temperature is of about 85° C. to about reflux temperature.

33. The process of claim 32, wherein the temperature is about reflux temperature.

34. The process of claim 30, wherein the base is sodium carbonate.

35. The process of claim 30, wherein the base is added portion-wise.

36. A process for preparing ziprasidone comprising the steps of reacting BITP or a salt thereof with CEI, and recovering the ziprasidone, wherein the reacting is carried out with sodium carbonate decahydrate at a temperature greater than melting point of sodium carbonate decahydrate but lower than melting point of sodium carbonate anhydrous.

37. The process of any of claims 1, 9, 16, 24, 30 or 36 wherein ziprasidone is converted to a pharmaceutically acceptable salt thereof.

* * * * *

UNITED STATES PATENT AND TRADEMARK OFFICE
CERTIFICATE OF CORRECTION

| | | |
|---|---|---|
| PATENT NO. | : 7,667,037 B2 | Page 1 of 1 |
| APPLICATION NO. | : 10/973498 | |
| DATED | : February 23, 2010 | |
| INVENTOR(S) | : Pilarsky et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 708 days.

Signed and Sealed this

Seventh Day of December, 2010

David J. Kappos
*Director of the United States Patent and Trademark Office*